US007135013B2

(12) United States Patent
Olson et al.

(10) Patent No.: US 7,135,013 B2
(45) Date of Patent: Nov. 14, 2006

(54) HIGH SWELL ABSORBENT CHANGING A THIN UNDERPANTS-LIKE GARMENT INTO A THICK DIAPER-LIKE GARMENT

(75) Inventors: Christopher Peter Olson, Neenah, WI (US); Lawrence Howell Sawyer, Neenah, WI (US); Shirlee Ann Weber, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 487 days.

(21) Appl. No.: 10/027,798

(22) Filed: Dec. 20, 2001

(65) Prior Publication Data
US 2003/0139713 A1 Jul. 24, 2003

(51) Int. Cl.
*A61F 13/15* (2006.01)
(52) U.S. Cl. .............................. 604/385.101; 604/378; 604/368
(58) Field of Classification Search ......... 604/385.101, 604/378, 385.01, 379, 380, 385.23, 385.16, 604/385.17, 361, 385.12, 367
See application file for complete search history.

(56) References Cited

U.S. PATENT DOCUMENTS

| 5,702,376 | A  | * | 12/1997 | Glaug et al. ................ 604/361 |
| 6,168,585 | B1 | * | 1/2001  | Cesco-Cancian ....... 604/385.26 |
| 6,191,340 | B1 | * | 2/2001  | Carlucci et al. ............ 604/369 |
| 6,509,959 | B1 |   | 1/2003  | Hamajima et al. |

FOREIGN PATENT DOCUMENTS

| CN | 1153465 A   | 7/1997 |
| WO | WO 95/18589 | 7/1995 |

* cited by examiner

*Primary Examiner*—Jacqueline F Stephens
(74) *Attorney, Agent, or Firm*—Pauley Petersen & Erickson

(57) ABSTRACT

A pant-like absorbent garment having a swellable absorbent core positioned between an outer cover and a body side liner at least partially bonded to the outer cover. The swellable absorbent core is swellable to a final thickness ($t_f$) which is at least three times an initial thickness ($t_i$) of the swellable absorbent core; $t_f \geq 3 t_i$. The significant swelling renders the garment suitable for use as a toilet training aid.

49 Claims, 5 Drawing Sheets

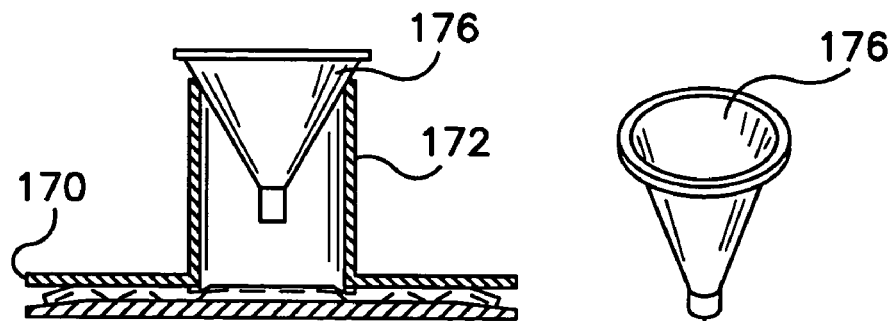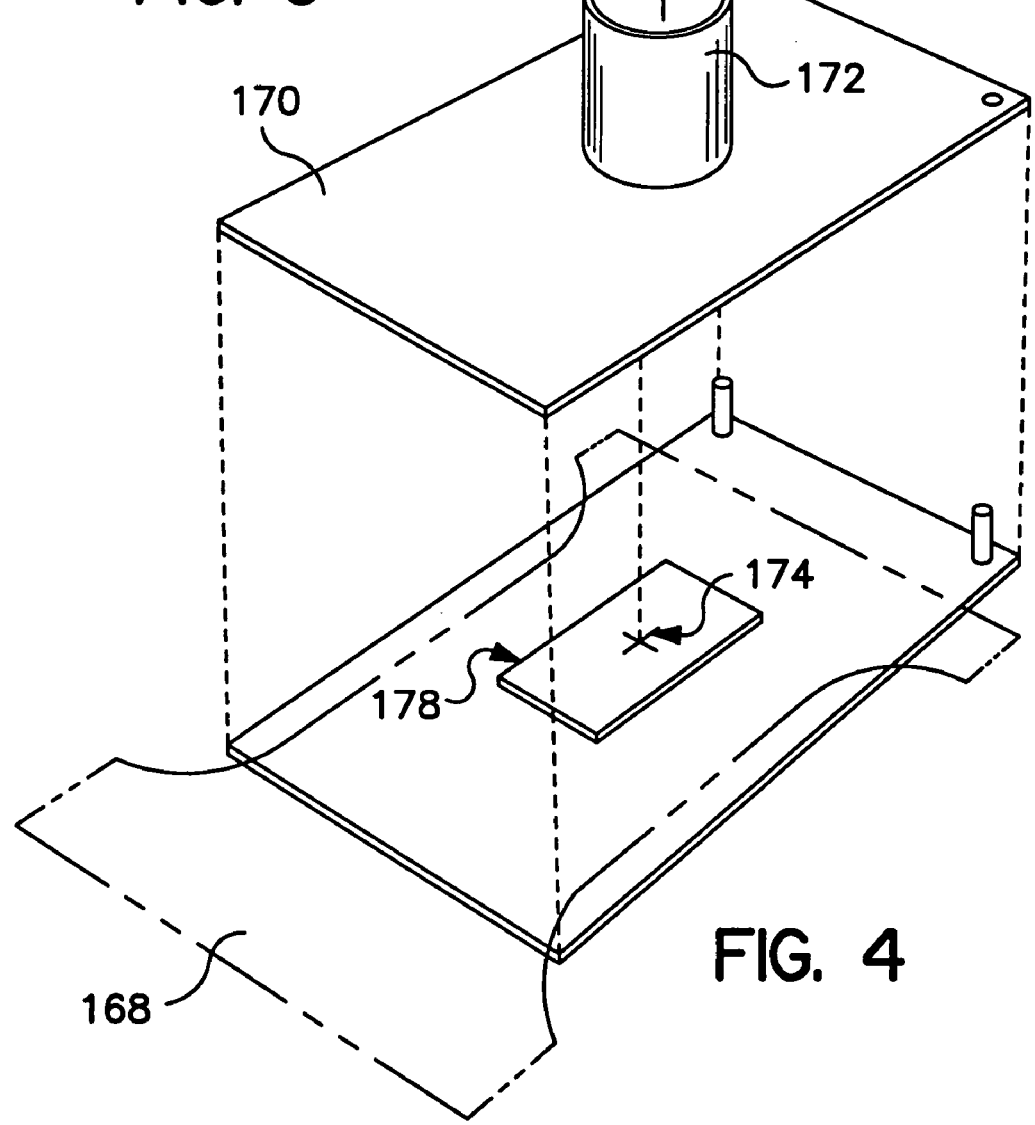

HIGH SWELL ABSORBENT CHANGING A THIN UNDERPANTS-LIKE GARMENT INTO A THICK DIAPER-LIKE GARMENT

BACKGROUND OF THE INVENTION

This invention is directed to pant-like, personal care absorbent garments having an absorbent core that swells significantly as it absorbs a liquid insult, for example urine.

Toilet training a child is often not an easy task and thus training aids are commonly employed to help in training. However, many parents have found that conventional training pants, as well as conventional diapers, are unsuccessful in motivating their child to become toilet trained.

Some conventional highly absorbent training pants and diapers generally are so effective in absorbing insults, for example urine, that the child does not know when he or she is wearing a wet garment. This can confuse a child and possibly delay toilet training. Many parents believe that a wet sensation or a change in feeling experienced by the child during or after urination will discourage the child from wetting his or her garment and will help him or her complete toilet training.

Further, some conventional garments, for example training pants, closely resemble conventional diapers. Many parents believe that if a child cannot distinguish a training pant from a conventional diaper, he or she will not be motivated to keep his or her training pant dry.

There is a need or desire for a toilet training garment that motivates a child to complete the toilet training process.

There is a need or desire for a single insult disposable training pant that is capable of absorbing only one urination and must be changed after each urination, whereby a child wearing the training pant feels and is aware that the training pant is wet or feels different after urination.

SUMMARY OF THE INVENTION

The present invention is directed to pant-like disposable absorbent garments or articles, for example single insult training pants, having a swellable absorbent core that swells significantly as the absorbent core absorbs a liquid insult, such as urine. The garment can be used as a toilet training aid. The garment is thin when dry, like typical underwear. If the wearer wets the pant, the pant protects and becomes thick and diaper-like. The wearer experiences the consequences of converting their "big kid underwear" into a baby diaper. This combination of reward and consequence can help motivate children to toilet train. The concept is simple and straightforward so it is easy for a toddler to understand.

The pant-like disposable absorbent article includes an absorbent core positioned or located between an outer cover and a body side liner which is connected to the outer cover in a superposed relation. Desirably, the swellable absorbent core is made of a relatively thin, high swelling absorbent material such as an extremely thin, high swelling absorbent composite material or an ultra-thin-absorbent (UTA) material including a mixture of superabsorbent material and pulp fiber.

According to one embodiment of this invention, the absorbent assembly swells during absorption of the first insult to create a void area in the absorbent assembly which enhances uptake and fluid distribution during a possible subsequent insult, even though the product is designed for a single use. In this embodiment, the garment is thin and discreet and close to the body when dry. Yet the garment has the ability to deploy a thicker absorbent after the first insult. The thicker absorbent gives the garment the volume needed to handle large insults only when such volume is needed, i.e. after the first insult. The increased thickness alerts the wearer of the need to change the garment while the void area provides containment of any subsequent insults that occur before the soiled garment can be replaced.

The swellable absorbent product assembly desirably has an initial dry thickness less than about 3.0 mm, more desirably less than about 2.5 mm, and still more desirably less than about 2.0 mm. The swellable absorbent product assembly has an overall or total absorbent capacity desirably not greater than about three times an anticipated insult volume, more desirably not greater than about two times an anticipated insult volume, and thus is suitably capable of accommodating an insult having a volume of about 30 grams (g) to about 100 g, desirably about 60 g to about 80 g. In certain embodiments, the swellable absorbent product assembly can accommodate an insult volume of grater than about 100 g, if desired. Suitably, the swellable absorbent product assembly has an overall absorbent capacity of about 300 g or less, such as about 30 g to about 300 g, desirably about 40 g to about 240 g, alternatively about 50 g to about 200 g.

An absorbent core suitably has an initial dry thickness ($t_i$) of less than about 2.0 mm, more suitably less than about 1.5 mm, most suitably less than about 1.0 mm, and is swellable upon an insult, at least in a region of the insult, to a final wet thickness ($t_f$) desirably at least about three times greater than the initial dry thickness of the absorbent core, more desirably at least about five times greater than the initial dry thickness of the absorbent core. For example, in one embodiment of this invention, the absorbent core may have an initial dry thickness of about 0.60 mm to about 0.85 mm. Upon absorbing an insult having a volume of about 80 g, the absorbent core may swell or expand to a final wet thickness greater than about 3.75 mm. Suitably, the absorbent core has an overall absorbent capacity of greater than about 100 g, desirably about 130 g to about 200 g, alternatively about 140 g to about 180 g.

With the foregoing in mind, particular embodiments of the invention provide a pant-like absorbent garment having an absorbent core which swells significantly, at least in a target region or zone, as the absorbent core absorbs an insult such as urine.

Additionally, particular embodiments of the invention, provide a single insult training pant for use as a motivational training aid for toilet training a child whereby the child experiences the consequence of the swelling of the absorbent core upon insult.

BRIEF DESCRIPTION OF THE DRAWINGS

FIG. 4 is an exploded perspective view of a testing apparatus used to measure fluid intake and flowback;

FIG. 5 is a side elevational view showing the apparatus of FIG. 4 in operation;

DEFINITIONS

Figure 1:
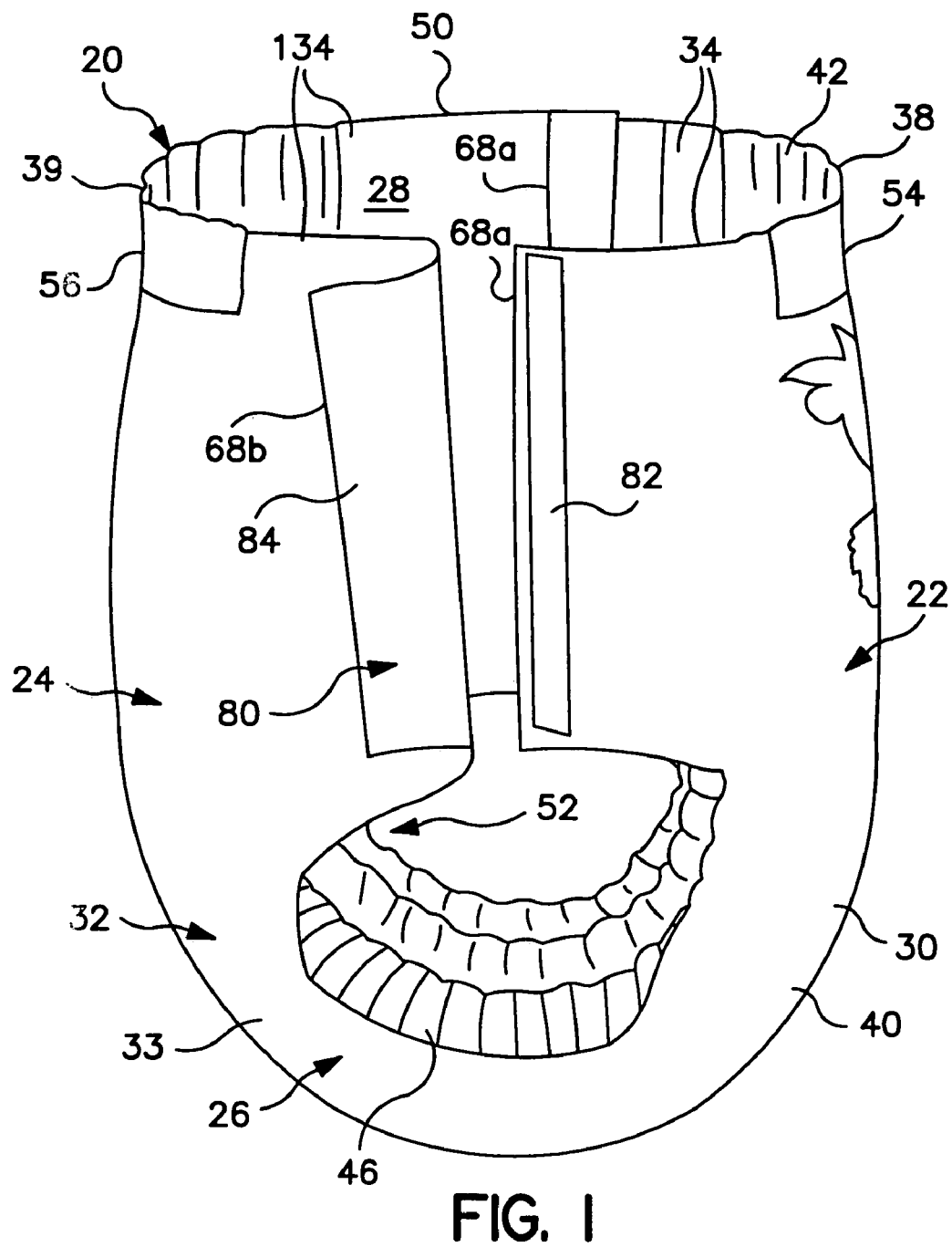
FIG. 1 is a side perspective view of an absorbent garment having a swellable absorbent core, according to one embodiment of this invention.

Within the context of this specification, each term or phrase below will include the following meaning or meanings.

"Absorbent core" refers to a liquid storage material in an absorbent product assembly.

"Anticipated insult volume" refers to a volume of fluid, for example urine, which the swellable absorbent product assembly is able to accommodate. Suitably, in accordance with one embodiment of this invention, the anticipated insult volume is about 30 g to about 100 g, desirably about 60 g to about 80 g. In certain embodiments, the swellable absorbent product assembly is able to accommodate an insult volume of greater than about 100 g, if desired.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Connected" refers to the joining, adhering, bonding, attaching, or the like, of two elements. Two elements will be considered to be connected together when they are connected directly to one another or indirectly to one another, such as when each is directly connected to intermediate elements.

"Disposable" refers to garments or articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover a high percentage, such as about seventy five percent, of its original size and shape after removal of a force causing a deformation.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Fabrics" is used to refer to all of the woven, knitted and nonwoven fibrous webs.

"Film" refers to a thermoplastic film made using a film extrusion and/or foaming process, such as a cast film or blown film extrusion process. The term includes apertured films, slit films, and other porous films which constitute liquid transfer films, as well as films which do not transfer or conduct liquid.

"High swelling absorbent material" describes an absorbent material that swells or thickens to a final wet thickness at least 3 times greater than an initial dry thickness upon absorption of sufficient amounts of liquid, for example urine.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "nonwettable" or hydrophobic.

"Integral" or "integrally" is used to refer to various portions of a single unitary element rather than separate structures bonded to or placed with or placed near one another.

"Layer" when used in the singular can have the dual meaning of a single element or a plurality of elements.

"Liquid impermeable" when used to describe a layer or laminate means that liquid, such as urine, will not pass through the layer or laminate under ordinary use conditions in a direction generally perpendicular to the plane of the layer or laminate at the point of liquid contact.

"Liquid permeable" refers to a layer or laminate that is not liquid impermeable.

Figure 2:
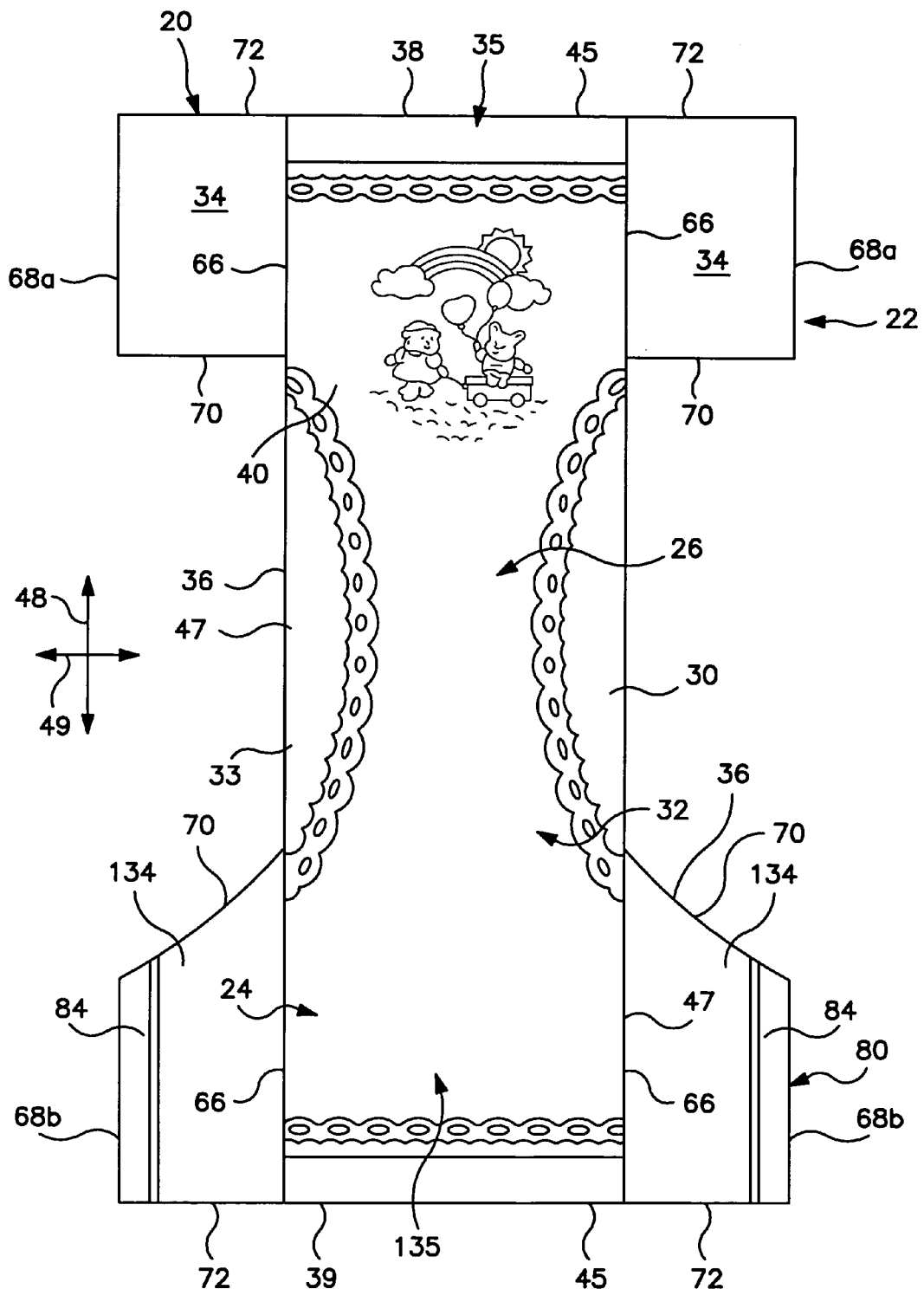
FIG. 2 is a plan view of the absorbent garment of FIG. 1 in a partially disassembled, stretched flat state, and showing the surface of the garment that faces away from the wearer when the garment is worn, according to one embodiment of this invention.
Figure 3:
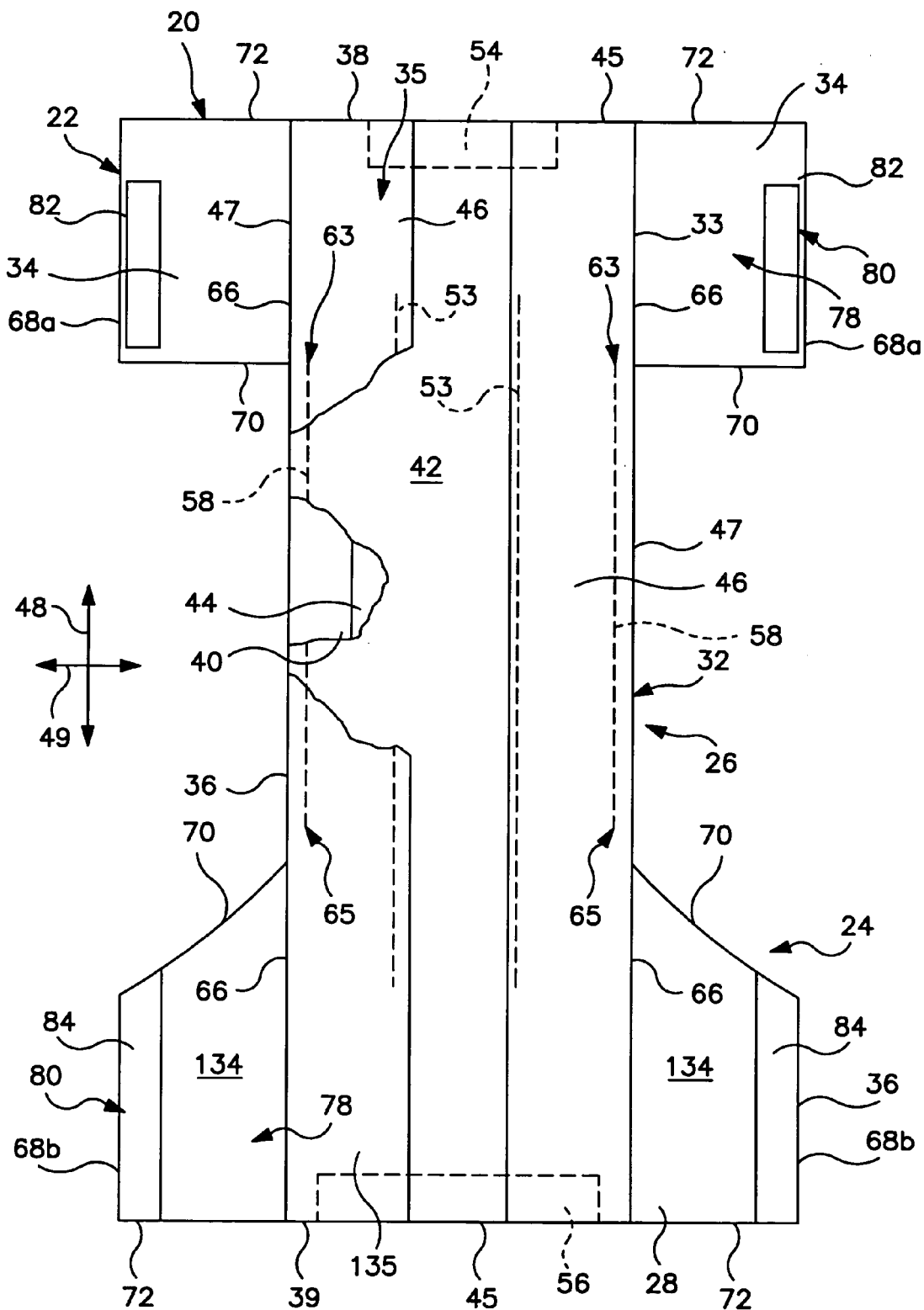
FIG. 3 is a plan view of the absorbent garment of FIGS. 1 and 2 in a partially disassembled, stretched flat state, and showing the surface of the garment that faces the wearer when the article is worn, and with portions cut away to show the underlying features, according to one embodiment of this invention.

"Longitudinal" and "transverse" have their customary meaning, as indicated by the longitudinal and transverse axes depicted in FIGS. 2 and 3. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Meltblown fiber" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers can be macrofibers or microfibers that may be continuous or discontinuous. They are generally smaller than about 0.6 denier, but can be greater than about 25 denier, and are generally self bonding when deposited onto a collecting surface. Meltblown fibers used in the present invention are preferably substantially continuous in length.

"Member" when used in the singular can have the dual meaning of a single element or a plurality of elements.

"Nonwoven" and "nonwoven web" refer to materials and webs of material which are formed without the aid of a textile weaving or knitting process.

"Operatively joined," in reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Permanently bonded" refers to the joining, adhering, connecting, attaching, or the like, of two elements of an absorbent garment such that the elements tend to be and remain bonded during normal use conditions of the absorbent garment.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Refastenable" refers to the property of two elements being capable of releasable attachment, separation, and subsequent releasable reattachment without substantial permanent deformation or rupture.

"Spunbonded fiber" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Stretchable" means that a material can be stretched, without breaking, to at least 150% of its initial (unstretched) length in at least one direction, suitably to at least 200% of its initial length, desirably to at least 250% of its initial length.

"Superabsorbent" or "superabsorbent material" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

A "surface" is formed by the interface between two compositions of matter, one of which may be air, and can include any layer, film, woven, nonwoven, laminate, composite, or the like, whether pervious or impervious to air, gas, and/or liquids.

"Thermoplastic" describes a material that softens when exposed to heat and which substantially returns to a non-softened condition when cooled to room temperature.

"Void volume" describes a space encompassed by a material or a portion of a material forming a zone or region which is capable of collecting and storing voided material, such as urine.

These terms may be defined with additional language in the remaining portions of the specification.

DETAILED DESCRIPTION OF THE INVENTION

The present invention is directed to a pant-like absorbent garment having an absorbent core which swells significantly as the absorbent core absorbs an insult, for example urine. The absorbent core can be an effective training aid when toilet training children. Further, in one embodiment of this invention, the swelling of the absorbent core during a first insult creates a void area in the absorbent core that enhances intake and fluid distribution during subsequent insults. The principles of the present invention can be incorporated into any suitable disposable absorbent article. Examples of such suitable articles include diapers, training pants, feminine hygiene products, incontinence products, other personal care or health care garments, or the like. For ease of explanation, the description hereafter will be in terms of a child's training pant.

Referring to FIG. 1, a pant-like disposable absorbent garment or article, such as a training pant 20, is illustrated in a partially fastened condition. The training pant 20 includes an absorbent chassis 32 and a fastening system 80. The absorbent chassis 32 defines a front region 22, a back region 24, a crotch region 26 interconnecting the front and back regions, an inner surface 28 which is configured to contact the wearer, and an outer surface 30 opposite the inner surface which is configured to contact the wearer's clothing. As shown in further detail in FIGS. 2 and 3, the absorbent chassis 32 also defines a pair of transversely opposed side edges 36 and a pair of longitudinally opposed waist edges, which are designated front waist edge 38 and back waist edge 39. The front region 22 is contiguous with the front waist edge 38, and the back region 24 is contiguous with the back waist edge 39.

The illustrated absorbent chassis 32 includes a generally rectangular composite structure 33, a pair of transversely opposed front side panels 34, and a pair of transversely opposed back side panels 134. The composite structure 33 and side panels 34 and 134 may be integrally formed, as shown in FIG. 1, or may include two or more separate elements, as shown in FIGS. 2 and 3. The illustrated composite structure 33 includes an outer cover 40, a bodyside liner 42 which is connected to the outer cover in a superposed relation, and an absorbent core 44 (FIG. 3) which is positioned or located between the outer cover 40 and the bodyside liner 42. The composite structure 33 may also include a pair of containment flaps 46, as shown in FIG. 3. The rectangular composite structure 33 has opposite linear or curvilinear end edges 45 that form portions of the front and back waist edges 38 and 39, and opposite linear side edges 47 that form portions of the side edges 36 of the absorbent chassis 32 (FIGS. 2 and 3). For reference, arrows 48 and 49 depicting the orientation of the longitudinal axis and the transverse axis, respectively, of the training pant 20 are illustrated in FIGS. 2 and 3. Alternatively, the composite structure 33 can have an irregular shape such as an hourglass or with a wider front center panel 35. The dimensions of the absorbent structure can range from a width of at least about 25 mm to about 75 cm, and a length that encompasses the same range. In certain embodiments, the width of the absorbent structure can be greater than 75 cm, if necessary.

With the training pant 20 in the fastened position as partially illustrated in FIG. 1, the front and back regions 22 and 24 are joined together to define a three-dimensional pant configuration having a waist opening 50 and a pair of leg openings 52. The front region 22 includes the portion of the training pant 20 which, when worn, is positioned on the front of the wearer while the back region 24 includes the portion of the training pant which, when worn, is positioned on the back of the wearer. The crotch region 26 of the training pant 20 includes the portion of the training pant which, when worn, is positioned between the legs of the wearer and covers the lower torso of the wearer. The front and back side panels 34 and 134 include the portions of the training pant 20 which, when worn, are positioned on the hips of the wearer.

The front region 22 of the absorbent chassis 32 includes the transversely opposed front side panels 34 and a front center panel 35 (FIGS. 2 and 3) positioned between and interconnecting the side panels, along with a front waist elastic member 54 and any other connected components. The back region 24 of the absorbent chassis 32 includes the transversely opposed back side panels 134 and a back center panel 135 (FIGS. 2 and 3) positioned between and interconnecting the side panels, as well as a rear waist elastic member 56 and any other connected components. The waist edges 38 and 39 of the absorbent chassis 32 are configured to encircle the waist of the wearer when worn and provide the waist opening 50 which defines a waist perimeter dimension. Portions of the transversely opposed side edges 36 in the crotch region 26 generally define the leg openings 52.

The absorbent chassis 32 is configured to contain and/or absorb any body exudates discharged from the wearer. For example, the absorbent chassis 32 desirably, although not necessarily, includes the pair of containment flaps 46 which are configured to provide a barrier to the transverse flow of body exudates. A flap elastic member 53 (FIG. 3) is operatively joined with each containment flap 46 in any suitable manner as is well known in the art. The elasticized containment flaps 46 define an unattached edge which assumes an upright, generally perpendicular configuration in at least the crotch region 26 of the training pant 20 to form a seal against the wearer's body. The containment flaps 46 can be located along the transversely opposed side edges of the absorbent chassis 32, and can extend longitudinally along the entire length of the absorbent chassis or may only extend partially along the length of the absorbent chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pant 20 desirably includes the front waist elastic member 54, the rear waist elastic member 56, and leg elastic members 58, as are known to those skilled in the art (FIG. 3). The waist elastic members 54 and 56 can be operatively joined to the outer cover 40 and/or bodyside liner 42 along the opposite waist edges 38 and 39, and can extend over part or all of the waist edges. The leg elastic members 58 are desirably operatively joined to the outer cover 40 and/or bodyside liner 42 along the opposite side edges 36 and positioned in the crotch region 26 of the training pant 20. The leg elastic members 58 are desirably longitudinally aligned along each side edge 47 of the composite structure 33. Each leg elastic member 58 has a front terminal point 63 and a back terminal point 65, which points represent the longitudinal ends of the elastic gathering caused by the leg elastic members. The front terminal points 63 are desirably located adjacent the longitudinally innermost parts of the front side panels 34, and the back terminal points 65 are desirably located adjacent the longitudinally innermost parts of the back side panels 134.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 58 include a plurality of dry-spun coalesced multifilament spandex elastomeric threads sold under the trade name LYCRA® and available from E. I. DuPont de Nemours and Company, Wilmington, Del., U.S.A.

The outer cover 40 desirably includes a material that is substantially liquid impermeable, and can be elastic, stretchable or nonstretchable. The outer cover 40 can be a single layer of liquid impermeable material, but desirably includes a multi-layered laminate structure in which at least one of the layers is liquid impermeable. For instance, the outer cover 40 can include a liquid permeable outer layer and a liquid impermeable inner layer that are suitably joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable bodyside liner 42 is made. While it is not a necessity for the outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and care giver. A suitable liquid impermeable film for use as a liquid impermeable inner layer, or a single layer liquid impermeable outer cover 40, is a 0.2 millimeter polyethylene film commercially available from Huntsman Packaging of Newport News, Va., U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

The liquid permeable bodyside liner 42 is illustrated as overlying the outer cover 40 and absorbent core 44, and may but need not have the same dimensions as the outer cover 40. The bodyside liner 42 is desirably compliant, soft feeling, and non-irritating to the wearer's skin. Further, the bodyside liner 42 can be less hydrophilic than the absorbent core 44, to present a relatively dry surface to the wearer and permit liquid to readily penetrate through its thickness.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.28 weight percent of a surfactant commercially available from the Rohm and Haas Co. under the trade designation Triton X-102. Other suitable surfactants are commercially available from Uniqema Inc., a division of ICI of New Castle, Del., under the trade designation Ahcovel, and from Cognis Corporation of Ambler, Pa., produced in Cincinnati, Ohio, and sold under the trade designation Glucopon 220. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal centerline.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. While the outer cover 40 and bodyside liner 42 can include elastomeric materials, it can be desirable in some embodiments for the composite structure to be generally inelastic, where the outer cover, the bodyside liner and the absorbent assembly include materials that are generally not elastomeric.

In accordance with one embodiment of this invention, the absorbent core 44, as shown in FIG. 3, is positioned or located between the outer cover 40 and the bodyside liner 42, which components can be joined together by any suitable means, such as adhesives, as are well known in the art. The absorbent core 44 is a high swelling absorbent material which swells appreciably or significantly as the absorbent core 44 absorbs a liquid insult, for example urine. Desirably, the absorbent core 44 is relatively thin, having an initial dry thickness ($t_i$) of less than about 2.0 mm, more desirably having an initial dry thickness of less than about 1.5 mm, and still more desirably having an initial dry thickness of less than about 1.0 mm. Upon insult, the swellable absorbent core 44, at least in the area or zone of insult, absorbs the insult and swells to a final wet thickness ($t_f$) desirably at least about three times greater than the initial dry thickness, more desirably at least about five times greater than the initial dry thickness. The increased thickness makes the training pant 20 look and feel more like a diaper to the wearer and encourages the wearer to replace the garment with a dry training pant 20, as well as encourage training.

In one embodiment of this invention, the swelling of the absorbent core 44 as a result of the first insult creates a void area in the absorbent core 44 that enhances uptake and fluid distribution during subsequent insults.

The training pant 20 can in particular embodiments have an overall or total absorbent capacity not greater than about three times an anticipated insult volume, more desirably not greater than about two times the anticipated insult volume, and a high saturated capacity, making the absorbent core 44 a very efficient absorbent structure. In one embodiment of this invention, a single void training pant 20 for children between about 18 months and about 48 months old, suitably accommodates an insult having a volume of about 30 grams (g) to about 100 g, desirably about 60 g to about 80 g. In certain embodiments of this invention, the training pant 20 may accommodate insult volumes of greater than about 100 g if desired.

The overall absorbent capacity of the absorbent core 44 is expressed in terms of grams (g) of fluid absorbed (and retained). Desirably, the overall absorbent capacity of the absorbent core 44 can in particular embodiments be greater than about 100 g, more desirably about 130 g to about 200 g, and still more desirably about 140 g to about 180 g. The saturated capacity (i.e. absorbent efficiency) of the absorbent core 44 is expressed in terms of grams (g) of fluid retained/ gram (g) of absorbent structure, wherein a higher value represents a greater efficiency. Desirably, the saturated capacity of the absorbent core 44 is greater than about 7 g/g, more desirably about 9 g/g to about 11 g/g, and still more desirably greater than about 12.0 g/g. Both overall absorbent capacity and saturated capacity of the absorbent core 44 are determined by a saturated capacity test, discussed below.

For example, an absorbent core 44 comprising a fluff pulp and superabsorbent material, as well as other components, is able to retain a specific amount of fluid that is determined by the individual fluid capacities of the components and their relative percentages within the absorbent core 44. The superabsorbent (SAP) material is highly efficient, whereas the fluff pulp material is moderately efficient. Further, some synthetic fibers such as polyester fibers are generally inefficient. An "efficient" absorbent structure will retain a relatively large volume of fluid, whereas an "inefficient" absorbent structure will retain a relatively small volume of fluid.

The absorbent core 44 can be any structure which is generally compressible, conformable, non-irritating to the wearer's skin, and capable of absorbing and retaining liquids and certain body wastes. The absorbent core 44 can be manufactured in a wide variety of sizes and shapes, and from a wide variety of liquid absorbent materials commonly used in the art. For example, the absorbent core 44 can suitably include a matrix of hydrophilic fibers, such as a web of cellulosic fluff, mixed with particles of a high-absorbency material commonly known as superabsorbent material. In a particular embodiment, the absorbent core 44 includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be nonuniformly mixed. The fluff and superabsorbent particles can also be selectively placed into desired zones of the absorbent core 44 to better contain and absorb body exudates. The concentration of the superabsorbent particles can also vary through the thickness of the absorbent core 44. Alternatively, the absorbent core 44 can include a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

Desirably, the swellable absorbent core 44 is made of a relatively thin, high swelling absorbent material such as an extremely thin, high swelling absorbent composite material sold under the trade name NOVATHIN® available from EAM Corporation located in Jessup, Ga., U.S.A. or an ultra-thin-absorbent (UTA) material including a mixture of SAP and pulp fiber, for example 3.7 g of Favor SXM 9543 SAP, available from Stockhausen GmbH & Co. KG located in Krefeld, Fed. Rep. of Germany, and 3.7 g of NB416 pulp fiber available from Weyerhaeuser located in Federal Way, Wash., or 2.9 g of Favor SXM 9543 SAP and 6.7 g of NB416 pulp fiber, cut or formed in a roughly 100 mm by 385 mm rectangular pad. Suitable materials for the absorbent core 44 include those materials described in U.S. patent application Ser. No. 09/939,061, filed on Aug. 24, 2001, the disclosure of which is incorporated herein by reference.

In one embodiment, the absorbent core 44 is generally rectangular in shape, and includes a blend of wood pulp fluff and superabsorbent material. One preferred type of fluff is identified with the trade designation CR1654, available from U.S. Alliance, Childersburg, Ala., U.S.A., and is a bleached, highly absorbent sulfate wood pulp containing primarily soft wood fibers. Suitable As a general rule, the superabsorbent material is present in the absorbent core 44 in an amount of from about 0 to about 90 weight percent based on total weight of the absorbent core 44. The absorbent core 44 suitably has a density within the range of about 0.10 to about 0.50 grams per cubic centimeter. The absorbent core 44 may or may not be wrapped or encompassed by a suitable tissue wrap that maintains the integrity and/or shape of the absorbent core 44.

The absorbent chassis 32 can also incorporate other materials that are designed primarily to receive, temporarily store, and/or transport liquid along the mutually facing surface with the absorbent core 44, thereby maximizing the overall absorbent capacity of the absorbent core 44, if desired. One suitable material is referred to as a surge layer (not shown) and includes a material having a basis weight of about 50 to about 120 grams per square meter, and including a through-air-bonded-carded web of a homogenous blend of 60 percent 3 denier type T-256 bicomponent fiber including a polyester (PET) core/polyethylene sheath and 40 percent 6 denier type T-295 polyester (PET) fiber, both commercially available from Kosa Corporation of Salisbury, N.C., U.S.A.

As noted previously, the illustrated training pant 20 has front and back side panels 34 and 134 disposed on each side of the absorbent chassis 32. These transversely opposed front side panels 34 and transversely opposed back side panels 134 can be permanently bonded to the composite structure 33 of the absorbent chassis 32 in the respective front and back regions 22 and 24. Additionally, the side panels 34 and 134 can be permanently bonded to one another using suitable bonding means, such as adhesive bonds or ultrasonic bonds, to provide a non-refastenable training pant 20. Alternatively, the side panels 34 and 134 can be releasably attached to one another by a fastening system 80. More particularly, as shown best in FIGS. 2 and 3, the front side panels 34 can be permanently bonded to and extend transversely beyond the linear side edges 47 of the composite structure 33 in the front region 22 along attachment lines 66, and the back side panels 134 can be permanently bonded to and extend transversely beyond the linear side edges of the composite structure in the back region 24 along attachment lines 66. The side panels 34 and 134 may be attached using attachment means known to those skilled in the art such as adhesive, thermal or ultrasonic bonding. The side panels 34 and 134 can also be formed as a portion of a component of the composite structure 33, such as the outer cover 40 or the bodyside liner 42.

In particular embodiments for improved fit and appearance, the side panels 34 and 134 desirably have an average length dimension measured parallel to the longitudinal axis 48 that is about 20 percent or greater, and particularly about 25 percent or greater, of the overall length dimension of the absorbent article, also measured parallel to the longitudinal axis 48. For example, in training pants having an overall length dimension of about 54 centimeters, the side panels 34 and 134 desirably have an average length dimension of about 10 centimeters or greater, such as about 15 centimeters. While each of the side panels 34 and 134 extend from the waist opening 50 to one of the leg openings 52, the back side panels 134 have a continually decreasing length dimension moving from the attachment line 66 to a distal edge 68b of the back panel 134, as is best shown in FIGS. 2 and 3.

Each of the side panels 34 and 134 can include one or more individual, distinct pieces of material. In particular embodiments, for example, each side panel 34 and 134 can include first and second side panel portions that are joined at a seam, with at least one of the portions including an elastomeric material. Still alternatively, each individual side panel 34 and 134 can include a single piece of material which is folded over upon itself along an intermediate fold line (not shown).

The side panels 34 and 134 desirably include an elastic material capable of stretching in a direction generally parallel to the transverse axis 49 of the training pant 20. In particular embodiments, the front and back side panels 34 and 134 may each include an interior portion 78 disposed between the distal edge 68a, 68b and the respective front or back center panel 35 or 135. In the illustrated embodiment in FIG. 3, the interior portions 78 are disposed between the distal edges 68a, 68b and the side edges 47 of the rectangular composite structure 33. The elastic material of the side panels 34 and 134 can be disposed in the interior portions 78 to render the side panels elastomeric in a direction generally parallel to the transverse axis 49. Most desirably, each side panel 34 and 134 is elastomeric from a waist end edge 72 to a leg end edge 70. More specifically, individual samples of side panel material, taken between the waist end edge 72 and the leg end edge 70 parallel to the transverse axis 49 and having a length from the attachment line 66 to the distal edge 68a, 68b and a width of about 2 centimeters, are all elastomeric.

Suitable elastic materials, as well as one described process of incorporating elastic side panels into a training pant, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material includes a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al., all of which are incorporated herein by reference. Alternatively, the side panel material may include other woven or nonwoven materials, such as those described above as being suitable for the outer cover 40 or bodyside liner 42, or stretchable but inelastic materials.

The training pant 20 according to the present invention also includes a fastening system 80 for securing the training pant about the waist of the wearer (FIG. 1). In on embodiment, the fastening system 80 can permanently fasten side panels 34 and 134 to form the training pant 20. More desirably, referring to FIGS. 1–3, the fastening system 80 includes fastening components 82 that are adapted to refastenably connect to mating fastening components 84. In one embodiment, one surface of each of the fastening components 82 and 84 includes a plurality of engaging elements that project from that surface. The engaging elements of these fastening components 82 are adapted to repeatedly engage and disengage the engaging elements of the mating fastening components 84.

In one particular embodiment, the fastening components 82 each include hook type fasteners and the mating fastening components 84 each include complementary loop type fasteners. In another particular embodiment, the fastening components 82 each include loop type fasteners and the mating fastening components 84 each include complementary hook type fasteners. The fastening components 82 and the mating fastening components 84 are desirably rectangular, although they may alternatively be square, round, oval, curved or otherwise non-rectangularly shaped.

Loop type fasteners typically include a fabric or material having a base or backing structure and a plurality of loop members extending upwardly from at least one surface of the backing structure. The loop material can be formed of any suitable material, such as acrylic, nylon or polyester, and can be formed by methods such as warp knitting, stitch bonding or needle punching. Suitable loop materials are available from Guilford Mills, Inc., Greensboro, N.C., U.S.A. under the trade designation No. 36549.

Hook type fasteners typically include a fabric or material having a base or backing structure and a plurality of hook members extending upwardly from at least one surface of the backing structure. In contrast to the loop type fasteners which desirably include a flexible fabric, the hook material advantageously includes a resilient material to minimize unintentional disengagement of the fastener components as a result of the hook material becoming deformed and catching on clothing or other items. The term "resilient" as used herein refers to an interlocking material having a predetermined shape and the property of the interlocking material to resume the predetermined shape after being engaged and disengaged from a mating, complementary interlocking material. Suitable hook material can be molded or extruded of nylon, polypropylene or another suitable material. Suitable single-sided hook materials for the fastening components 82 or the mating fastening components 84 are available from Velcro Industries B.V., Amsterdam, Netherlands or affiliates thereof, and are identified as Velcro HTH-829 with a unidirectional hook pattern and having a thickness of about 0.089 millimeters (3.5 mils) and HTH-851 with a uni-directional hook pattern and having a thickness of about 0.051 millimeters (2 mils).

The absorbent chassis 32 and the fastening system 80 together define a refastenable product having a waist opening 50 and a pair of leg openings 52. When the fastening system is engaged, the refastenable product includes a pair of front side panels 34 extending from the waist opening 50 to each leg opening 52, a pair of back side panels 134 extending from the waist opening 50 to each leg opening 52, an elastomeric front waistband 54 disposed on the front side 22 and positioned between the pair of front side panels 34, an elastomeric back waistband 56 disposed on the back side 24 and positioned between the pair of back side panels 134, and at least a pair of the leg elastic members 58 which partially encircle each leg opening 52. More preferably, more than one leg elastic member 58 partially or fully encircles each leg opening 52. Each leg elastic member 58 extends from adjacent a front side panel 34 on the front side 22 to adjacent a back side panel 134 on the back side 24.

As described herein, the various components of the absorbent garment 20 can be integrally assembled together employing various types of suitable attachment means, such as adhesive, sonic and thermal bonds or combinations thereof.

The resulting product is an absorbent garment that swells significantly when wet and can be used as a toilet training aid.

EXAMPLES

Single insult training pants (CODE 1A, CODE 1B and CODE 2) were produced in accordance with embodiments of this invention comprising a swellable absorbent core. The swellability of the absorbent core of each training pant produced according to this invention was compared to the swellability of absorbent cores of conventional training pants (CODE 3 and CODE 4) using a modified Fluid-Intake and Flowback Evaluation (FIFE) Test Method. The initial dry thickness ($t_i$) and the final wet thickness ($t_f$) of each absorbent core was measured. The results of the modified FIFE test are displayed below in Tables 1–5.

In accordance with one embodiment of this invention, a single insult training pant was produced including an absorbent core comprising an ultra-thin-absorbent (UTA) material including 3.7 g of Favor SXM 9543 SAP and 3.7 g of NB416 pulp fiber (CODE 1A). The absorbent core had a width of about 100 mm and a length of about 385 mm. Five samples of CODE 1A had an average initial dry thickness ($t_i$) of about 0.84 mm. The absorbent core was positioned between a body side liner comprising 0.5 osy spunbond material and an outer cover. A surge material comprising 50 gsm 6 denier PET/3 denier bicomponent binder fiber was placed between the absorbent core and the bodyside liner. The single insult training pant had a 0.5 psi overall absorbent capacity of about 150 g. After absorbing an 80 ml saline insult, the five samples of the absorbent core had an average final wet thickness ($t_f$) of about 4.40 mm. Thus, the final wet thickness ($t_f$) was greater than five times thicker than the initial dry thickness ($t_i$); $t_f \geq 5 t_i$.

In accordance with one embodiment of this invention, a single insult training pant was produced including an absorbent core comprising an ultra-thin-absorbent (UTA) material including 2.9 g of Favor SXM 9543 SAP, available from Stockhausen, Greensboro, N.C., U.S.A., and 6.7 g of NB416 pulp fiber, available from Weyerhaeuser Corporation, Tacoma, Wash., U.S.A. (CODE 1B). The absorbent core had a width of about 100 mm and a length of about 385 mm. Five samples of CODE 1B had an average initial dry thickness ($t_i$) of about 0.86 mm. The absorbent core was positioned between a body side liner comprising 0.5 osy spunbond material and an outer cover. A surge material comprising 50 gsm 6 denier PET/3 denier bicomponent binder fiber was placed between the absorbent core and the bodyside liner. The single insult training pant had a 0.5 psi overall absorbent capacity of about 150 g. After absorbing an 80 ml saline insult, the five samples of the absorbent core had an average final wet thickness ($t_f$) of about 4.31 mm. Thus, the final wet thickness ($t_f$) was greater than five times thicker than the initial dry thickness ($t_i$); $t_f \geq 5 t_i$.

In accordance with one embodiment of this invention, a single insult training pant, CODE 2, was produced comprising an absorbent core consisting of an absorbent material supplied by EAM Corporation. A surge material comprising 50 gsm 6 denier PET/3 denier bicomponent binder fiber was placed over the absorbent core in a target zone. The absorbent core had a width of about 102 mm, a length of about 385 mm. Five samples of CODE 2 absorbent core had an initial dry thickness ($t_i$) of about 0.62 mm. The absorbent core and the surge layer were positioned between a body side liner comprising 0.5 osy spunbond material and an outer cover. The single insult training pant had a 0.5 psi overall absorbent capacity of about 150 g. After absorbing an 80 ml saline insult, the five samples of the absorbent core had an average final wet thickness ($t_f$) of about 3.75 mm. Thus, the final wet thickness ($t_f$) was greater than six times thicker than the initial dry thickness ($t_i$); $t_f \geq 6 t_i$.

CODE 3 is a PULL-UPS® Training Pant manufactured in the U.S.A. by Kimberly-Clark Corporation, Neenah, Wis.

CODE 4 is a TOREPAN MAN® Pant manufactured by Unicharm, Japan.

Modified Fluid-Intake and Flowback Evaluation (FIFE) Test Method

An apparatus shown in FIGS. 4 and 5 is utilized for this test. The sample to be tested is shown in phantom as reference numeral 168 in FIG. 4. For commercially available products (CODE 3 and CODE 4), the absorbent core was removed and tested using the methods for testing Codes 1A, 1B and 2.

The sample 168 is first tested for dry thickness by placing the intake zone of the absorbent structure underneath a 0.2 psi weight, and the thickness of the absorbent in this region is recorded. A suitable tester for absorbent thickness is a MITUTOYO 543 Series thickness gauge, available from Mitutoyo-MTI Corporation, Japan, equipped with a 3 inch diameter brass foot that applies a weight of 0.2 psi. The sample 168 to be tested is then placed flat and smooth under an 880 gram cylinder plate assembly 170 such that the cylinder 172, which has a 5.1 centimeter inner diameter, is aligned with a longitudinal center line, over the center 174 of intake zone 178 of the absorbent structure. A funnel 176 weighting approximately 13.7 grams, with a ¼ inch (6.25 mm) outlet spout, may be used in the top of cylinder 172. Alternatively, test liquid as described below may be added directly into the cylinder 172.

Eighty milliliters of 0.9% w/v sodium chloride solution, available from Ricca Chemical Co., Arlington, Tex., U.S.A., is poured rapidly into the funnel 176 or directly into cylinder 172 and allowed to completely enter the absorbent sample, as judged visually by the tester. At the moment the fluid first appears fully absorbed, a five minute timer is started and the sample is allowed to stand for this time period. At the end of five minutes, the cylinder plate assembly 170 is removed and a wet thickness measurement is made on the zone of the absorbent that was centered inside the cylinder 172. The same method is used for the wet thickness measurement as was used for the dry thickness measurement. At least four specimens of each sample are tested, and the averages of the dry and wet thickness measurements, respectively, are determined. If a wet sample loses integrity so that unsupported transport to a thickness tester is not possible, a thin poly film may be employed under specimens to relocate them. The thickness of the poly film should be subtracted from the total measured thickness of the supported sample to determine the absorbent composite thickness.

Modified FIFE Test Results

TABLE 1

CODE 1A: UTA PROTOTYPE at 80 ml
50% Favor SXM 9543, 50% NB416

| Sample | Dry Pant Wt. | Initial Thickness, $t_i$ (mm) | Final Thickness, $t_f$ (mm) |
|---|---|---|---|
| 1 | 9.48 | 0.81 | 4.40 |
| 2 | 9.40 | 0.83 | 4.40 |
| 3 | 9.44 | 0.86 | 4.46 |
| 4 | 9.74 | 0.87 | 4.36 |
| 5 | 8.96 | 0.84 | 4.38 |
| Avg. | 9.40 | 0.84 | 4.40 |

TABLE 2

CODE 1B: UTA PROTOTYPE at 80 ml
2.9 grams Favor SXM 9543, 6.7 grams NB416

| Sample | Dry Pant Wt. | Initial Thickness, $t_i$ (mm) | Final Thickness, $t_f$ (mm) |
|---|---|---|---|
| 1 | 11.65 | 0.91 | 4.47 |
| 2 | 11.45 | 0.83 | 4.38 |
| 3 | 11.28 | 0.89 | 4.00 |
| 4 | 11.78 | 0.84 | 3.89 |
| 5 | 11.84 | 0.84 | 4.80 |
| Avg. | 11.60 | 0.86 | 4.31 |

TABLE 3

CODE 2: EAM PROTOTYPE at 80 ml

| Sample | Dry Pant Wt. | Initial Thickness, $t_i$ (mm) | Final Thickness, $t_f$ (mm) |
|---|---|---|---|
| 1 | 7.83 | 0.61 | 3.40 |
| 2 | 8.34 | 0.63 | 3.81 |
| 3 | 8.81 | 0.64 | 4.05 |
| 4 | 8.11 | 0.62 | 3.84 |
| 5 | 7.68 | 0.62 | 3.63 |
| Avg. | 8.15 | 0.62 | 3.75 |

TABLE 4

CODE 3: PULL-UPS ® Training Pant at 80 ml

| Sample | Dry Pant Wt. | Initial Thickness, $t_i$ (mm) | Final Thickness, $t_f$ (mm) |
| --- | --- | --- | --- |
| 1 | 33.8 | 4.44 | 10.48 |
| 2 | 32.4 | 4.67 | 9.32 |
| 3 | 33.2 | 4.16 | 11.40 |
| 4 | 33.3 | 4.47 | 10.88 |
| 5 | 32.2 | 4.65 | 9.85 |
| Avg. | 33.0 | 4.48 | 10.39 |

TABLE 5

CODE 4: UNICHARM TOREPAN MAN ® 9–14 Kg. Pant at 80 ml

| Sample | Dry Pant Wt. | Initial Thickness, $t_i$ (mm) | Final Thickness, $t_f$ (mm) |
| --- | --- | --- | --- |
| 1 | 10.61 | 3.33 | 2.99 |
| 2 | 10.08 | 3.42 | 2.82 |
| 3 | 11.56 | 3.39 | 3.23 |
| 4 | 11.13 | 3.44 | 3.12 |
| Avg. | 10.85 | 3.40 | 3.04 |

Modified Saturated Capacity Test Method

Figure 6:
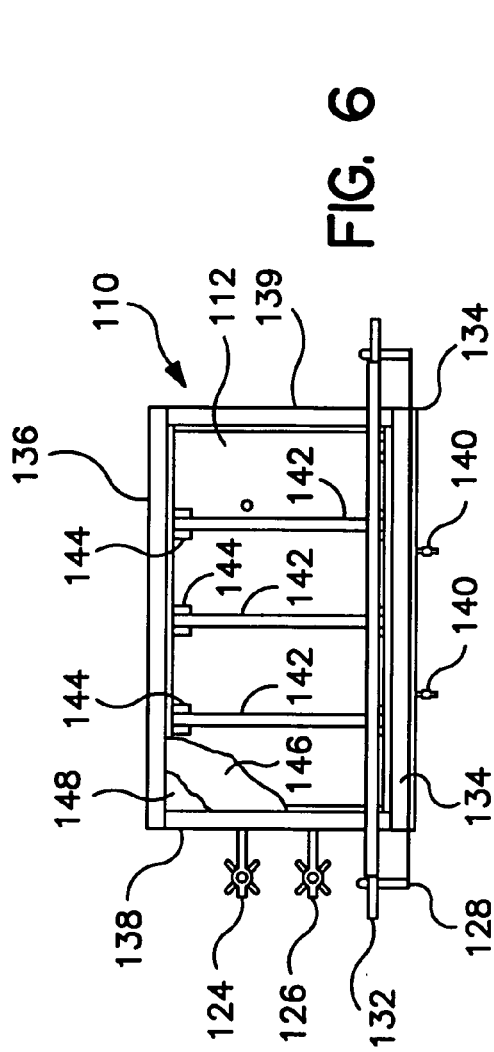
FIG. 6 representatively shows a partially cut away top view of a saturated capacity tester.
Figure 8:
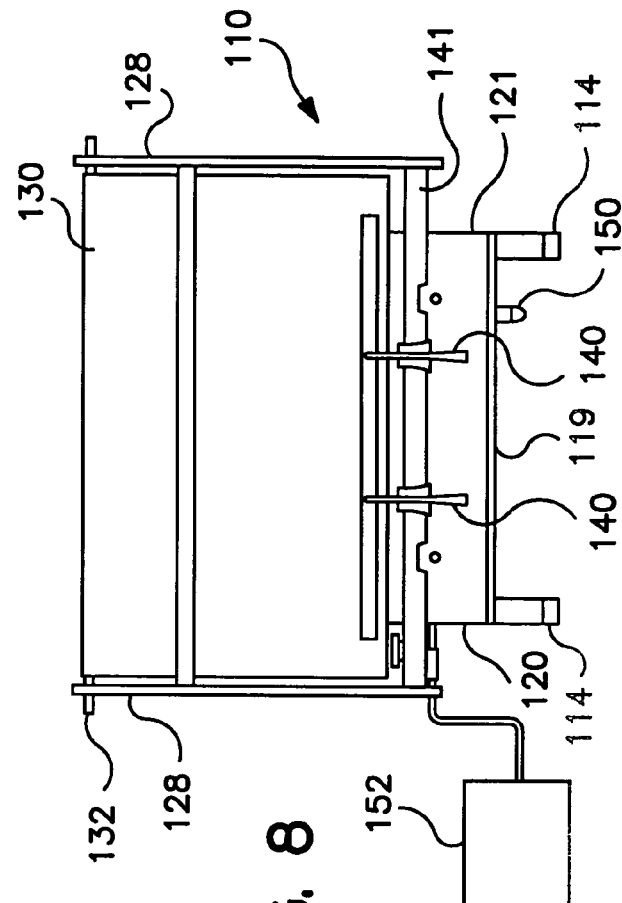
FIG. 8 representatively shows a rear view of a saturated capacity tester.
Figure 7:
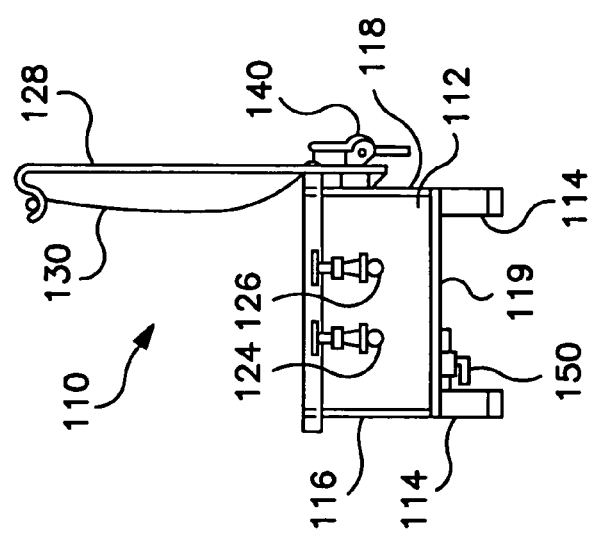
FIG. 7 representatively shows a side view of a saturated capacity tester.

Saturated Capacity is determined using a Saturated Capacity (SAT CAP) tester with a Magnahelic vacuum gage and a latex dam. Referring to FIGS. 6–8, a Saturated Capacity tester vacuum apparatus 110 comprises a vacuum chamber 112 supported on four leg members 114. The vacuum chamber 112 includes a front wall member 116, a rear wall member 118 and two side walls 120 and 121. The wall members are about 0.5 inch thick, and are constructed and arranged to provide a chamber having outside dimensions measuring 23.5 inches in length, 14 inches in width and 8 inches in depth.

A vacuum pump (not shown) operably connects with the vacuum chamber 112 through an appropriate vacuum line conduit and a vacuum valve 124. In addition, a suitable air bleed line connects into the vacuum chamber 112 through an air bleed valve 126. A hanger assembly 128 is suitably mounted on the rear wall 118 and is configured with S-curved ends to provide a convenient resting place for supporting a latex dam sheet 130 in a convenient position away from the top of the vacuum apparatus 110. A suitable hanger assembly can be constructed from 0.25 inch diameter stainless steel rod. The latex sheet 130 is looped around a dowel member 132 to facilitate grasping and to allow a convenient movement and positioning of the latex sheet 130. In the illustrated position, the dowel member 132 is shown supported in a hanger assembly 128 to position the latex sheet 130 in an open position away from the top of the vacuum chamber 112.

A bottom edge of the latex sheet 130 is clamped against a rear edge support member 134 with suitable securing means, such as toggle clamps 140. The toggle clamps are mounted on the rear wall member 118 with suitable spacers 141 which provide an appropriate orientation and alignment of the toggle clamps 140 for the desired operation. Three support shafts 142 are 0.75 inches in diameter and are removably mounted within the vacuum chamber 112 by means of support brackets 144. The support brackets 144 are generally equally spaced along the front wall member 116 and the rear wall member 118 and arranged in cooperating pairs. In addition, the support brackets 144 are constructed and arranged to suitably position the uppermost portions of the support shafts 142 flush with the top of the front, rear and side wall members of the vacuum chamber 112. Thus, the support shafts 142 are positioned substantially parallel with one another and are generally aligned with the side wall members 120 and 121. In addition to the rear edge support member 134, the apparatus 110 includes a front support member 136 and two side support members 138 and 139. Each side support member measures about 1 inch in width and about 1.25 inches in height. The lengths of the support members are constructed to suitably surround the periphery of the open top edges of the vacuum chamber 112, and are positioned to protrude above the top edges of the chamber wall members by a distance of about 0.5 inches.

A layer of egg crating type material 146 is positioned on top of the support shafts 142 and the top edges of the wall members of the vacuum chamber 112. For example, the egg crating type material can be a translucent light diffuser panel available from McMaster Supply Catalog No. 162 4K 14, having a 13 mm by 13 mm opening in the panel. The egg crating type material extends over a generally rectangular area measuring 23.5 inches by 14 inches, and has a depth measurement of about 0.38 inches. The individual cells of the egg crating structure measure about 0.5 inch square, and the thin sheet material comprising the egg crating is composed of a suitable material, such as polystyrene. A layer of 0.19 mesh nylon screening 148, which measures 23.5 inches by 14 inches, is placed on top of egg crating material 146. Desirably, the mesh nylon screening is a TEFLON-coated, 6 mm mesh nylon screening available from Eagle Supply & Plastic, Inc., Part No. 7308.

A suitable drain line and a drain valve 150 connect to bottom plate member 119 of the vacuum chamber 112 to provide a convenient mechanism for draining liquids from the vacuum chamber 112. The various wall members and support members of tester apparatus 110 may be composed of a suitable noncorroding, moisture-resistant material, such as polycarbonate plastic. The various assembly joints may be affixed by solvent welding, and the finished assembly of the tester is constructed to be watertight. A vacuum gauge 152 operably connects through a conduit into the vacuum chamber 112. A suitable pressure gauge is a Magnahelic differential gauge capable of measuring a vacuum of 0–100 inches of water, such as a No. 2100 gauge available from Dwyer Instrument Incorporated.

The dry product or other absorbent structure is weighed and then placed in an excess amount of 0.9% saline solution and allowed to soak for 20 minutes. After the 20 minute soak time, the absorbent structure is placed on the egg crate material and mesh nylon screening of the Saturated Capacity tester. The latex sheet is placed over the absorbent structure(s) and the entire egg crate grid so that the latex sheet creates a seal when a vacuum is drawn on the tester. A vacuum of 0.5 pounds per square inch (psi) is held in the Saturated Capacity tester for five minutes. The vacuum creates a pressure on the absorbent structure(s), causing drainage of some liquid. After five minutes at 0.5 psi vacuum, the latex sheet is rolled back and the absorbent structure(s) are weighed to generate a wet weight.

The overall capacity of each absorbent structure is determined by subtracting the dry weight of each absorbent from the wet weight of that absorbent determined at this point in the procedure. The 0.5 psi SAT CAP or SAT CAP of the absorbent structure is determined by the following formula:

$$\text{SAT CAP} = (\text{wet weight} - \text{dry weight})/\text{dry weight};$$

wherein the SAT CAP value has units of grams fluid/gram absorbent. For both overall capacity and SAT CAP, a minimum of three specimens of each sample should be tested and the results averaged. If the absorbent structure has low integrity or disintegrates during the soak or transfer procedures, the absorbent structure can be wrapped in a containment material such as paper toweling, for example Hi-Dri® paper towels manufactured by Kimberly-Clark Corporation, Neenah, Wis., U.S.A. The absorbent structure can be tested with the overwrap in place and the capacity of the overwrap can be independently determined and subtracted from the wet weight of the total wrapped absorbent structure to obtain a wet absorbent weight.

MODIFIED SATURATED CAPACITY TEST RESULTS

TABLE 6

CODE 1A: UTA PROTOTYPE

50% Favor SXM 9543, 50% NB416

| Sample | Dry Weight of Product | Wet Weight After 20 Min. Soak | Amount Absorbed (Wet Wt. − Dry Wt.) | Saturated Capacity (g/g), (Amount Absorbed/Dry Wt.) |
|---|---|---|---|---|
| 1 | 12.86 | 157.15 | 144.29 | 11.2 |
| 2 | 12.62 | 150.51 | 137.89 | 10.9 |
| 3 | 13.16 | 156.06 | 142.90 | 10.9 |
| Avg. | 12.88 | 154.57 | 141.69 | 11.0 |

TABLE 7

CODE 1B: UTA PROTOTYPE 2.9 grams Favor SXM 9543, 6.7 grams NB416

| Sample | Dry Weight of Product | Wet Weight After 20 Min. Soak | Amount Absorbed (Wet Wt. − Dry Wt.) | Saturated Capacity (g/g), (Amount Absorbed/Dry Wt.) |
|---|---|---|---|---|
| 1 | 15.34 | 164.90 | 149.36 | 9.8 |
| 2 | 15.33 | 166.00 | 150.67 | 9.8 |
| 3 | 15.08 | 164.11 | 149.03 | 9.9 |
| Avg. | 15.25 | 165.00 | 149.75 | 9.8 |

TABLE 8

CODE 2: EAM PROTOTYPE

| Sample | Dry Weight of Product | Wet Weight After 20 Min. Soak | Amount Absorbed (Wet Wt. − Dry Wt.) | Saturated Capacity (g/g), (Amount Absorbed/Dry Wt.) |
|---|---|---|---|---|
| 1 | 14.31 | 171.90 | 157.59 | 11.0 |
| 2 | 14.19 | 172.49 | 158.30 | 11.2 |
| 3 | 13.84 | 162.85 | 149.01 | 10.8 |
| Avg. | | | | |

TABLE 9

CODE 3: PULL-UPS ® Training Pant

| Sample | Dry Weight of Product | Wet Weight After 20 Min. Soak | Amount Absorbed (Wet Wt. − Dry Wt.) | Saturated Capacity (g/g), (Amount Absorbed/Dry Wt.) |
|---|---|---|---|---|
| 1 | 36.16 | 603.77 | 567.61 | 15.7 |
| 2 | 35.89 | 578.86 | 542.97 | 15.1 |
| 3 | 36.28 | 542.97 | 550.27 | 15.2 |
| Avg. | | | | |

TABLE 10

CODE 4: UNICHARM TOREPAN MAN ® 9–14 Kg. Pant

| Sample | Dry Weight of Product | Wet Weight After 20 Min. Soak | Amount Absorbed (Wet Wt. − Dry Wt.) | Saturated Capacity (g/g), (Amount Absorbed/Dry Wt.) |
|---|---|---|---|---|
| 1 | 19.82 | 156.60 | 136.78 | 6.9 |
| 2 | 19.93 | 154.13 | 134.20 | 6.7 |
| 3 | 18.90 | 141.09 | 122.19 | 6.5 |
| 4 | 18.99 | 147.11 | 128.12 | 6.8 |
| Avg. | 19.41 | 149.73 | 130.32 | 6.7 |

TABLE 11

SUMMARY OF MODIFIED FIFE TEST RESULTS

| Product | Average Dry Absorbent Thickness ($t_i$) (mm) | Average Wet Absorbent Thickness after Insult ($t_f$) (mm) | Increase Over Dry Thickness ($t_f$)/($t_i$) |
|---|---|---|---|
| CODE 1A | 0.84 | 4.40 | 5.2 |
| CODE 2 | 0.62 | 3.75 | 6.0 |
| CODE 3 | 4.48 | 10.39 | 2.3 |
| CODE 4 | 3.40 | 3.04 | 0.9 |

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. A disposable training pant comprising:
   an absorbent chassis defining a front waist region, a back waist region and a crotch region interconnecting the front waist region and the back waist region;
   an outer cover;
   a bodyside liner at least partially bonded to the outer cover; and
   a swellable absorbent core positioned between the outer cover and the bodyside liner, the absorbent core having an overall absorbent capacity of about 130 grams to about 200 grams and an initial thickness ($t_i$), the absorbent core swellable to a final thickness ($t_f$), $t_f \geq 3t_i$, the disposable training pant having an overall absorbent capacity of about 300 g or less.

2. The disposable training pant of claim 1 wherein $t_f \geq 5t_i$.

3. The disposable training pant of claim 1 wherein the initial thickness is less than about 2.0 mm.

4. The disposable training pant of claim 1 wherein the initial thickness is less than about 1.5 mm.

5. The disposable training pant of claim 1 wherein the initial thickness is less than about 1.0 mm.

6. The disposable training pant of claim 1 wherein the initial thickness is about 0.5 mm to about 1.0 mm.

7. The disposable training pant of claim 1 wherein the absorbent article training pant has an initial thickness less than about 3.0 mm.

8. The disposable training pant of claim 1 wherein the training pant has an initial thickness less than about 2.5 mm.

9. The disposable training pant of claim 1 wherein the training pant has an initial thickness less than about 2.0 mm.

10. The disposable training pant of claim 1 wherein the absorbent core has a width of at least about 25 mm.

11. The disposable training pant of claim 1 wherein the absorbent core has a width of at least about 50 mm.

12. The disposable training pant of claim 1 wherein the absorbent core has a width of at least about 100 mm.

13. The disposable training pant of claim 1 wherein the absorbent core has a length of about 25 mm to about 700 mm.

14. The disposable training pant of claim 1 wherein the absorbent core has a length of about 250 mm to about 600 mm.

15. The disposable training pant of claim 1 wherein the absorbent core has a length of about 300 mm to about 550 mm.

16. The disposable training pant of claim 1 wherein the absorbent core has an overall absorbent capacity of about 140 g to about 180 g.

17. The disposable training pant of claim 1 wherein the absorbent core comprises a high swelling absorbent material.

18. The disposable training pant of claim 1 further comprising a surge layer placed over the absorbent core.

19. A disposable training pant comprising:
an absorbent chassis having a front waist region and a back waist region joined to define a pant configuration having a waist opening and a pair of leg openings, and an outer cover and a bodyside liner which is connected to the outer cover in a superposed relation; and
an absorbent core located between the outer cover and the bodyside liner, the absorbent core having a total absorbent capacity of about 130 grams to about 200 grams and not greater than about three times an anticipated insult volume;
the absorbent core being swellable upon an insult to a final wet thickness at least about three times greater than an initial dry thickness of the absorbent core.

20. The disposable training pant of claim 19 wherein the final wet thickness is at least about five times greater than the initial dry thickness.

21. The disposable training pant of claim 19 wherein the initial dry thickness is less than about 2.0 mm.

22. The disposable training pant of claim 19 wherein the initial dry thickness is less than about 1.5 mm.

23. The disposable training pant of claim 19 wherein the initial dry thickness is less than about 1.0 mm.

24. The disposable training pant of claim 19 wherein the initial dry thickness is about 0.5 mm to about 1.0 mm.

25. The disposable training pant of claim 19 wherein the initial dry thickness is about 0.60 mm to about 0.85 mm.

26. The disposable training pant of claim 19 wherein the final wet thickness is greater than about 3.75 mm.

27. The disposable training pant of claim 19 wherein the training pant has an initial thickness less than about 3.0 mm.

28. The disposable training pant of claim 19 wherein the training pant has an initial thickness less than about 2.5 mm.

29. The disposable training pant of claim 19 wherein the training pant has an initial thickness less than about 2.0 mm.

30. The disposable training pant of claim 19 wherein the absorbent core has a width of at least about 25 mm.

31. The disposable training pant of claim 19 wherein the absorbent core has a width of at least about 50 mm.

32. The disposable training pant of claim 19 wherein the absorbent core has a width of at least about 100 mm.

33. The disposable training pant of claim 19 wherein the absorbent core has a length of about 25 mm to about 700 mm.

34. The disposable training pant of claim 19 wherein the absorbent core has a length of about 250 mm to about 600 mm.

35. The disposable training pant of claim 19 wherein the absorbent core has a length of about 300 mm to about 550 mm.

36. The disposable training pant of claim 19 wherein the absorbent core comprises a high swelling absorbent material.

37. A disposable training pant comprising:
an absorbent chassis defining a front waist region, a back waist region and a crotch region interconnecting the front waist region and the back waist region;
an outer cover;
a bodyside liner at least partially bonded to the outer cover;
a swellable absorbent core positioned between the outer cover and the bodyside liner, the absorbent core having an overall absorbent capacity of about 130 grams to about 200 grams and an initial thickness ($t_i$), the absorbent core swellable to a final thickness ($t_f$), whereby swelling of the absorbent core as a result of a first insult creates a void area in the swellable absorbent core that enhances uptake and fluid distribution during subsequent insults, and $t_f \geq 3t_i$,
the disposable training pant having an overall absorbent capacity of about 300 g or less.

38. The disposable training pant of claim 37 wherein $t_f \geq 5t_i$.

39. The disposable training pant of claim 37 wherein the initial thickness is less than about 2.0 mm.

40. The disposable training pant of claim 37 wherein the initial thickness is less than about 1.5 mm.

41. The disposable training pant of claim 37 wherein the initial thickness is less than about 1.0 mm.

42. The disposable training pant of claim 37 wherein the initial thickness is about 0.5 mm to about 1.0 mm.

43. The disposable training pant of claim 37 wherein the training pant has an initial thickness less than about 3.0 mm.

44. The disposable training pant of claim 37 wherein the training pant has an initial thickness less than about 2.5 mm.

45. The disposable training pant of claim 37 wherein the training pant has an initial thickness less than about 2.0 mm.

46. The disposable training pant of claim 37 wherein the absorbent core has a width of about 100 mm to about 400 mm.

47. The disposable training pant of claim 37 wherein the absorbent core has a length of about 100 mm to about 400 mm.

48. The disposable training pant of claim 37 wherein the absorbent core has an overall absorbent capacity of about 140 g to about 180 g.

49. The disposable training pant of claim 37 wherein the absorbent core comprises a high swelling absorbent material.

* * * * *